United States Patent [19]
Py

[11] Patent Number: 5,320,845
[45] Date of Patent: Jun. 14, 1994

[54] APPARATUS FOR DELIVERING MULTIPLE MEDICAMENTS TO AN EYE WITHOUT PREMIXING IN THE APPARATUS

[76] Inventor: Daniel Py, 9 Hampden St., Wellesley, Mass. 02181

[21] Appl. No.: 1,012

[22] Filed: Jan. 6, 1993

[51] Int. Cl.$^5$ .............................................. A61M 35/00
[52] U.S. Cl. ..................................... 424/427; 604/294; 604/295
[58] Field of Search ................. 604/294, 295; 424/427

[56] References Cited

U.S. PATENT DOCUMENTS

| Re. 33,801 | 1/1992 | Green | 222/82 |
|---|---|---|---|
| 2,778,360 | 1/1957 | Miskel | 128/218 |
| 3,411,503 | 11/1968 | Santomieri | 128/216 |
| 3,563,240 | 2/1971 | Silver | 128/234 |
| 3,595,439 | 7/1971 | Newby et al. | 222/80 |
| 3,684,136 | 8/1972 | Baumann | 222/386 |
| 3,718,139 | 2/1973 | Hanford | 128/235 |
| 3,731,853 | 5/1973 | Baumann et al. | 222/386 |
| 3,739,947 | 6/1973 | Baumann et al. | 222/136 |
| 3,756,390 | 9/1973 | Abbey et al. | 206/47 A |
| 4,516,969 | 5/1985 | Kintner | 604/187 |
| 4,623,337 | 11/1986 | Maurice | 604/298 |
| 4,639,248 | 1/1987 | Schweblin | 604/187 |
| 4,648,532 | 3/1987 | Green | 222/82 |
| 4,673,396 | 6/1987 | Urbaniak | 604/211 |
| 4,927,062 | 5/1990 | Walsh | 222/420 |
| 4,982,875 | 1/1991 | Pozzi et al. | 222/83 |
| 5,024,355 | 6/1991 | Jouillat et al. | 222/162 |
| 5,078,691 | 1/1992 | Hamacher | 604/191 |
| 5,085,651 | 2/1992 | Py | 604/294 |
| 5,163,929 | 4/1992 | Py | 604/294 |

Primary Examiner—Thurman K. Page
Assistant Examiner—Carlos Azpuru
Attorney, Agent, or Firm—Kenyon & Kenyon

[57] ABSTRACT

An apparatus for simultaneously delivering more than one kind of medicament to an eye, without premixing of the medicaments within the apparatus. The apparatus includes a special nozzle assembly which precludes reentry of medicament expelled from the nozzle to prevent commingling of the medicaments. In this way, dosages of two or more medicaments may be simultaneously delivered to an eye without the need for creating a stable premixture of the medicaments.

19 Claims, 2 Drawing Sheets

APPARATUS FOR DELIVERING MULTIPLE MEDICAMENTS TO AN EYE WITHOUT PREMIXING IN THE APPARATUS

BACKGROUND OF THE INVENTION

The present invention relates to an apparatus for dispensing fluid through a nozzle, such as an ocular treatment apparatus for applying medicament or other substances to an eye.

There are various known devices for applying medicament to the eye. A typical eye-drop container has a flexible vial and a nozzle for releasing drops of medicament into the eye by squeezing the vial. If the user squeezes too hard, too much medicament can be released and, as a result, drip down the user's cheek. There is typically no means provided for accurately controlling the volume of each dose of medicament released into the eye and the smallest drop obtained as a result of the combined effect of gravity and surface tension is always bigger than the space available on the eye for a drop. Also, if the tip of the nozzle becomes contaminated, there is typically no means provided for preventing the contaminated tip from contaminating the medicament within the vial, and thus possibly causing infection by use of the contaminated medicament. Because the medicament in such devices is typically exposed to air upon opening the nozzle, it is not desirable to use such devices to administer preservative-free formulations of medicament, other than by providing single-dose containers. The single-dose containers, however, are typically relatively expensive to package, particularly when used for prescription medications.

The foregoing problems are addressed for a single medicament by the apparatus for applying medicament to an eye which is the subject of my copending application Ser. No. 07/801,243 filed on Dec. 2, 1991. This apparatus comprises a medicament chamber for holding medicament, and a nozzle coupled in fluid communication with the medicament chamber. The nozzle defines a seam which is normally in a closed position for preventing the passage of medicament through the nozzle and which opens in response to the flow of medicament of sufficient pressure to permit the passage of the medicament through the nozzle for release into the eye.

A major advantage of this apparatus is that once a dose of medicament is released, the seam of the nozzle closes, and thus substantially prevents medicament which may have been exposed to air or foreign particles from passing back through the nozzle and into the apparatus, which can contaminate the remainder of medicament in the apparatus. However, the apparatus is not particularly suitable for simultaneously delivering two different medicaments.

Heretofore, in order to deliver two different products (e.g., an antibiotic and an anti-inflammatory drug) simultaneously, or two different drugs used concomitantly for glaucoma (e.g., a betablocker and pilocarpine), it has been necessary to formulate a mixture of the two medicaments. However, there are several problems associated with formulating mixtures. For example, the two drugs often have a different pH and different solubilities which make stable homogenous mixtures difficult or impossible to achieve. In addition, despite the fact that the two drugs may each have FDA approval, a combination of the two is considered to be a new drug which requires, as for a new drug, new pre-clinical and clinical studies, and a separate FDA approval. Moreover, it is often more difficult to obtain approval for the combination because the FDA requires a demonstration of a synergistic effect (i.e., that the combination is more effective than the added individual effectiveness of the drugs administered separately). The development and approval process together can take 7 to 10 years, even for the combination of two drugs already approved separately.

Other packages have been conceived to keep separate two products while on the shelf, and the mixture is to be reconstituted extemporaneously by the patient. But these "double reservoirs" still require a combined formulation for the duration of the treatment, and therefore they must satisfy the FDA regulations for combined products as mentioned previously. In addition, this type of reconstitution package can be very expansive to manufacture.

Yet another problem with the delivery of two different medicaments to an eye is that two ordinary sized drops results in an even greater excess of liquid in the conjunctival cul de sac than the excess which already results with a single drop. Consequently, even more medicament spills out of the eye as waste. For this reason, practitioners usually request their patients to add the two different drops 5 minutes apart. These instructions are frequently not followed by patients, resulting in complications due to the absence of one of the drugs. For example, in the case of Glaucoma, a first drop of medicament does not balance the intra-ocular pressure; only a combination with another drop of medicament will reduce the pressure to a normal level.

SUMMARY OF THE INVENTION

It is an object of the invention to provide an apparatus which can simultaneously deliver substantially predetermined volumes of two different medicaments into the eye each time the apparatus is actuated, without any prior commingling or mixing of the medicaments within the apparatus.

It is a further object of the invention to provide an apparatus which can deliver into an eye dosages of two preservative-free formulations of medicament or other substances, where each time a dose of fluid is released, the remainder of the fluid remains in a contaminant-free environment.

The apparatus of the invention includes an anterior double pump, a nozzle section and a posterior container section. The container is partitioned along its longitudinal axis into two separate compartments for holding two different medicaments without commingling. An anterior wall of the container section has a central stump which projects in the anterior direction to form a fluid tight seal to the posterior end of an inner nozzle forming member. The inner nozzle forming member partitions the pump section of the apparatus into two separate pump areas which communicate with the two separate compartments of the container section, respectively, through openings in the container anterior wall. Opposite sides of the inner nozzle forming member form fluid tight seals with the inner surface of the pump section of the container to prevent commingling of the medicaments in the respective pump areas.

An outer nozzle forming member encloses the pump areas and defines a nozzle with the inner nozzle forming member at the anterior tip of the apparatus. The inner nozzle forming member is received within the outer to define a tight interface therebetween which is ordinarily in a closed position for preventing the passage of medicament through the nozzle. The tight interface opens in response to the flow of medicament of sufficient pressure to permit the passage of the medicament through the nozzle for release into the eye. The outer nozzle forming member is made of a more flexible material in comparison to the inner nozzle forming member for facilitating the opening of the interface in response to the flow of medicament of sufficient pressure for release through the nozzle.

A pair of opposing piston members are arranged on opposite sides of the inner nozzle forming member for pressurizing the respective medicaments to flow through the interface between the nozzle forming members. The pistons are seated within respective piston cavities, each of which is coupled in fluid communication with the interface and with the medicament chamber in the pump section of the device. Each piston has a head which is fit within openings in the pump section wall to form a fluid tight seal therewith. Since the pump section wall is flexible, the piston heads may be compressed inward, driving the pistons toward the inner nozzle forming member and forcing the medicament in each piston cavity to open the tight interface between the inner and outer nozzle members whereby the medicament is forced out of the nozzle. Once the medicament is released, the interface between the inner and outer nozzle member immediately closes preventing any portion of medicament exposed to air from passing back into the nozzle where it would contaminate the remainder of the medicament in the apparatus. The rapid close of the nozzle also prevents any commingling of the two different medicaments in the device which would occur if part of the medicament were permitted to reenter through the nozzle.

As each piston is driven past the opening in the piston cavity which allows the cavity to communicate with its respective medicament chamber, the openings are blocked by the piston bodies thereby preventing any additional medicament from entering the piston cavity during actuation of the device. In this way, only the predetermined volume of medicament (i.e., dosage) in the respective piston cavities will be released. As pressure on the piston heads is released and the pistons return past the openings in the piston cavities, the suction effect will cause medicament from the medicament chambers to refill the piston cavities.

DETAILED DESCRIPTION OF THE INVENTION

Figure 1:
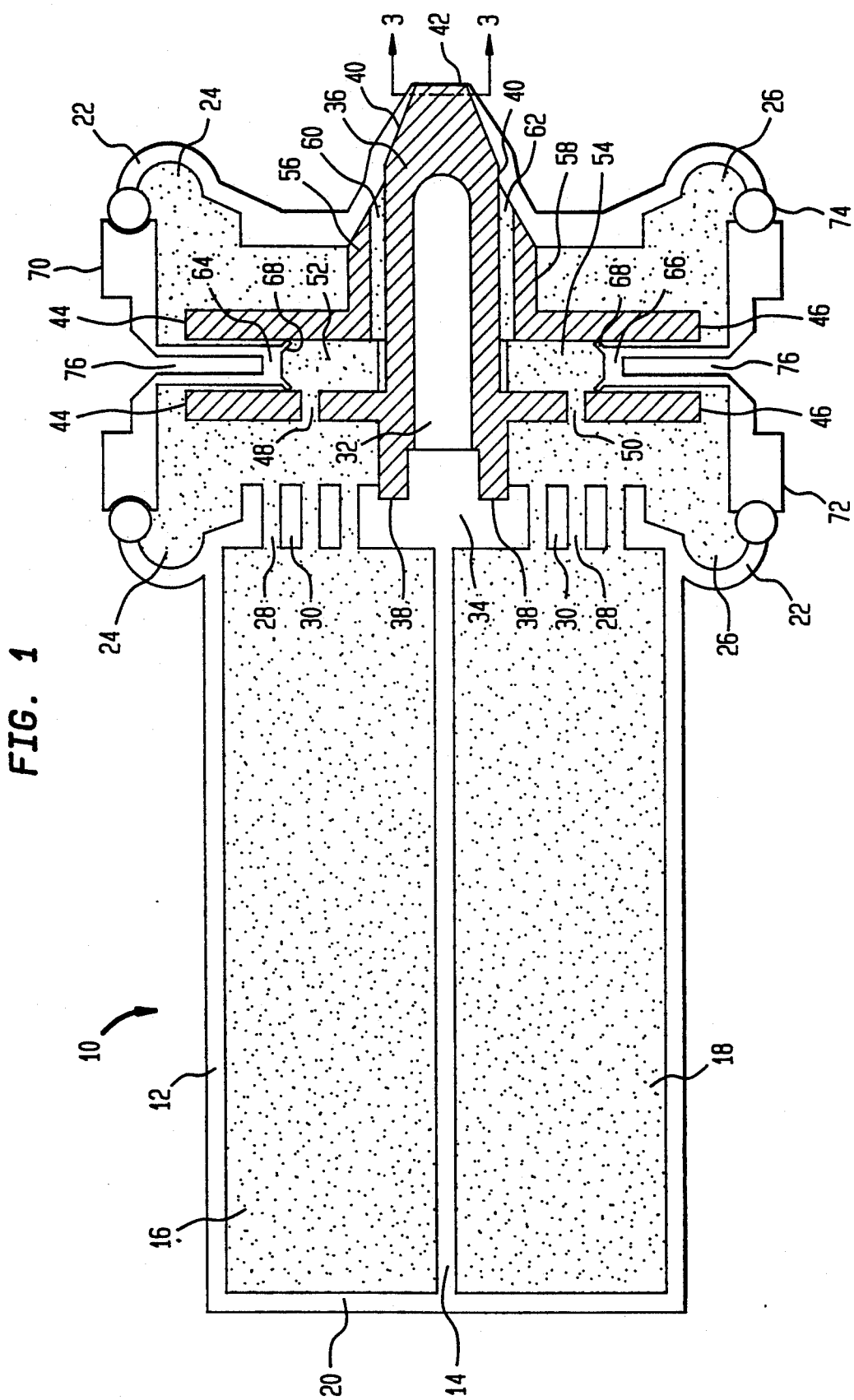
FIG. 1 is a cross-sectional view of an apparatus in accordance with the invention.
Figure 2:
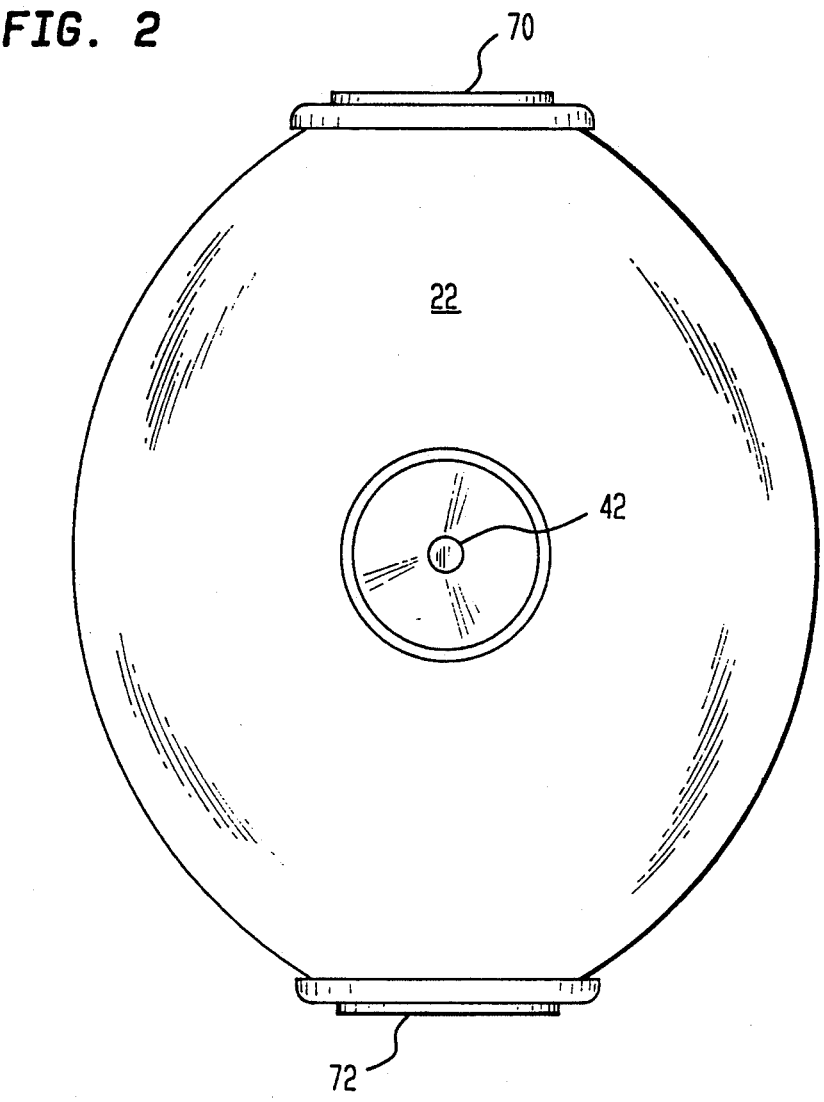
FIG. 2 is a head on view of the apparatus illustrated in FIG. 1.
Figure 3:
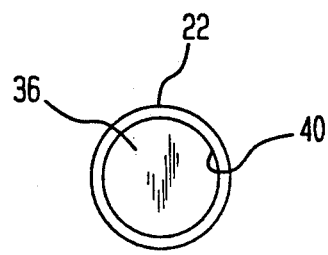
FIG. 3 is a cross-sectional view of the nozzle of the apparatus illustrated in FIG. 1 taken along the line 3—3 of FIG. 1.

Referring to FIG. 1, an apparatus in accordance with the present invention is indicated generally by the reference numeral 10. The apparatus includes a container or vial 12 which is compartmentalized by a partition wall 14 down its longitudinal axis into two separate chambers 16 and 18. The partition 14 is impermeable to liquids thereby allowing for storage of a different medicament in each container chamber 16, 18 without any commingling. The posterior end of the vial section 12 of the apparatus is closed off by a seal 20.

The anterior or pump section of the apparatus 10 is defined by an outer body wall 22 which encloses a pair of medicament chambers 24 and 26, disposed on opposite sides of the longitudinal axis. The medicament chamber 24 is in liquid communication with the vial chamber 16 through a plurality of apertures 28 in an anterior vial wall 30. Likewise, the medicament chamber 26 is in liquid communication with the vial chamber 18 through apertures 28. The medicament chambers 24 and 26 are separated by an inner nozzle forming body 36 which functions as a partition because it is connected to opposite sides of the inner surface of the outer body wall 22 to form a fluid tight seal therewith, thereby preventing commingling of medicament between the medicament chambers 24, 26.

Preferably, the inner nozzle forming body 36 has a bore 32 down its longitudinal axis for receiving the central section 34 of the wall 30. In this way, the plastic inner nozzle forming body 36 is inhibited from shrinking. Preferably, the central section 34 of the wall 30 is formed with an annular recess which receives a posterior annular flange 38 of the inner nozzle forming body 36 as illustrated in FIG. 1. The flange 38 forms a fluid tight seal with the central section 34 of the wall 30 and helps to firmly support the inner nozzle 36 in a fixed position in the apparatus.

The outer body wall 22 and the inner nozzle forming body 36 define a tight annular interface 40 therebetween at the anterior end of the apparatus 10. The inner nozzle forming body 36, the outer body wall 22 and the tight annular interface 40 taper toward the anterior tip of the device, and they terminate at the tip of the apparatus to define an annular nozzle 42 between the outer body wall 22 and the inner nozzle forming body.

The interface 40 and nozzle 42 are normally tightly closed, but are temporarily opened when medicament under sufficient pressure is forced through the interface 40 to be expelled through the nozzle. For this purpose, the outer body 22 is preferably molded from a relatively flexible plastic material in comparison to the inner body 36. Thus, the outer body 22 can be flexed relative to the inner nozzle forming body 36 to permit the passage of medicament through the interface 40 and out of the nozzle 42, as is described further below. In the embodiment of the present invention illustrated, the outer body 22 is preferably made of a thermoelastic plastic, such as the plastic sold under the name "Kraton" by the Shell Company. Preferably, the outer body wall 22, the partition wall 14, wall 30 and central section 34 are all molded as a single piece from Kraton. The inner body 36 is preferably made of a more rigid plastic, such as the plastic sold under the name "Valox", by the General Electric Company. These particular plastic materials are only exemplary, however, and other types of plastics can be used that are within the knowledge of those skilled in the art and which are gamma or beta stable for easier sterilization.

The inner nozzle forming body 36 includes a pair of lateral tubular flanges 44 and 46 which project laterally into medicament chambers 24 and 26, respectively. Slots 48 and 50 are formed in the posterior side of flanges 44 and 46, respectively, facing the anterior wall 30 of the vial. The lateral tubular flanges 44 and 46 define piston cavities 52 and 54, respectively, therein. The slots 48 and 50 allow for liquid communication between the piston cavities 52 and 54 with the medicament chambers 24 and 26, respectively.

Each lateral tubular flange 44, 46 includes a forwardly projecting flange 56 and 58, respectively, at its base on its anterior side which terminates at the outer body wall 22 to form a fluid tight seal therewith. The flanges 56 and 58 define channels 60 and 62, respectively, with the inner nozzle forming body 36 in the space therebetween. The channels 60 and 62 connect the piston cavities 52 and 54, respectively, with the tight interface 40 which leads to the nozzle 42. Therefore, the channels 60 and 62 taper at the point where they connect with the interface 40.

The tubular flanges 44 and 46 slidably receive pistons 64 and 66 in piston cavities 52 and 54, respectively. Each piston 64 and 66 has a flexible rim 68 on its free end which is adapted to be maintained in sliding contact with the inner surface of its respective tubular flange 44, 46. The rim 68 prevents medicament from passing beyond the point where it makes contact with the inner surface of the tubular flanges 44, 46 during piston strokes.

Each piston includes a piston disciform head 70 and 72. The peripheral edge of each disciform head is concave for tightly receiving a lobe 74 defined in the outer body wall 22. The lobe 74 snaps into the concave peripheral edge as illustrated in FIG. 1, supporting the pistons in the apparatus and forming a fluid tight seal. Each piston head 70, 72 preferably includes a bore 76 which extends partially down into the piston 64, 66 itself. If the apparatus is used with an external cartridge or other separate device for actuating the pistons, the bore will function to keep the pistons straight by receiving an external "hammer" which is part of the external cartridge. This has the advantage of reducing the amount of particulates which would ordinarily be generated by friction within the piston cavities during stroking of the pistons. However, use of an external cartridge as an accessory for holding and actuating the apparatus of the invention is not necessary and is merely optional.

With the pistons 64, 66 in their at rest position (i.e., up position), the piston cavities 52, 54 are adapted to hold a predetermined volume (e.g., a dosage) of medicament for release through the interface 40 and nozzle 42 into the eye. In the rest position, preferably the rim 68 of each piston is positioned just beyond the slots 48, 50 so that a significant amount of medicament in the piston cavities is not forced back into the medicament chambers 24, 26 during the downward stroke of the pistons. In predetermining the dosage volume to be expelled during actuation of the apparatus, one should factor in the extent to which the pistons 64, 66 cannot reach the surface of the inner nozzle body 36, which may result in some of the medicament in the piston cavities not being expelled. For example, it can be seen from FIG. 1 that the downward stroke of the pistons will be limited by the piston heads 70, 72 reaching the lateral tubular flanges 44, 46 so that the pistons 64, 66 cannot reach the inner nozzle member 36.

Each dosage cavity 52, 54 is preferably dimensioned to hold preferably 10 microliters of medicament, so that the total amount of the two drugs released will not exceed 20 microliters to avoid exceeding eye capacity and spillage of excess from the eye. However, this capacity is purely exemplary, and can be changed as desired.

As previously stated, the outer body wall 22 is constructed of a relatively flexible material. Upon applying downward pressure to the piston heads 70, 72, the outer body wall 22 will flex permitting the downward stroke of the pistons 64, 66 in the direction toward the inner nozzle forming body 36. As the medicament cannot traverse the contact area between the rim 68 of each piston and the inner surface of each tubular flange 44, 46, during the downward stroke of the pistons with sufficient pressure, the medicament in the piston cavities 52, 54 will be forced toward the nozzle forming body 36 and through the channels 60, 62 to temporarily open the tight interface 40. In other words, the medicament under pressure will force the relatively thin-walled section of the outer body 22 around the interface 40 (compared to the remainder of the outer body 22) to expand or bulge temporarily as the medicament passes through the interface 40. When the medicament is finally expelled through the nozzle 42, the tight interface 40 rapidly closes, thereby preventing any medicament dangling on the tip of the apparatus from reentering the apparatus through the nozzle 42. In this way, contamination of fresh medicament in the apparatus is avoided. This allows for the use of preservative-free medicaments which cannot be used with a conventional multiple dose eye dropper. This is a major advantage of the invention.

It will also be appreciated that the rapid close of the interface 40 and nozzle 42 prevents commingling of the two medicaments from channels 60 and 62 in the apparatus itself. This is because the partition 32 or inner nozzle body 36 prevents commingling of the medicaments in the channels 60 and 62 until the point where the channels 60, 62 lead into the interface 40. Once the medicaments are expelled from the nozzle, the immediate close of the nozzle 42 and interface 40 prevents reentry of any dangling medicament and, hence, prevents commingling of medicament in the apparatus.

As will be recognized by those skilled in the art, one advantage of the apparatus of the invention is that a substantially predetermined volume of medicament can be released into an eye each time the apparatus is actuated. The predetermined volume released can be controlled by controlling the volume of the piston cavities, for example. Another advantage of the apparatus of the invention is that once a dose of medicament is released, the tight interface of the nozzle closes, and thus substantially prevents medicament which has been exposed to air or foreign particles from passing through the nozzle and into the apparatus, which can, in some instances, contaminate the remainder of the medicament in the apparatus or result in commingling of the two medicaments in the apparatus. This advantage is particularly important when storing multipledose quantities of preservative-free formulations of medicament or other substances within the apparatus.

Another advantage of the apparatus 10 is that it allows for the simultaneous delivery of two different medicaments, without any prior commingling thereof in the apparatus. Thus, it is not necessary to formulate a stable premixture of the two medicaments for storage in the container, which may be difficult or impossible. In addition, separate lengthy FDA approval for a combination of the two drugs may not be necessary.

What is claimed is:

1. An apparatus for applying medicaments to an eye, comprising:
   a vial;

a means for partitioning said vial into a first medicament chamber and a second medicament chamber which precludes commingling of medicament in the first chamber with medicament in the second chamber; and a nozzle coupled in fluid communication with the first and second medicament chambers, the nozzle defining a tight interface therein normally in a closed position which prevents passage of medicament through the nozzle and which opens in response to a flow of medicament of sufficient pressure to permit passage of said flow of medicament through the nozzle for release into the eye.

2. An apparatus as defined in claim 1, wherein the nozzle includes an outer nozzle forming member and an inner nozzle forming member received within the outer nozzle forming member and the interface is defined therebetween.

3. An apparatus as defined in claim 1, further comprising a first piston means for pressurizing medicament in the first chamber to flow through the interface for release into the eye and a second piston means for pressurizing medicament in the second chamber to flow through the interface for release into the eye.

4. An apparatus as defined in claim 3, wherein the first piston means is seated within a first piston cavity coupled in fluid communication with the interface and the first medicament chamber, and the second piston means is seated within a second piston cavity coupled in fluid communication with the interface and the second medicament chamber, and wherein the first and second piston means are moveable within the respective piston cavities to cause medicament within each piston cavity to flow through the interface for release into the eye.

5. An apparatus as defined in claim 4, wherein each piston cavity is dimensioned to release a predetermined volume of medicament into the eye.

6. An apparatus as defined in claim 4, wherein each piston cavity is coupled in fluid communication with the respective medicament chamber by at least one aperture, and each piston means causes the medicament within the respective piston cavities to flow through the interface upon passing the at least one aperture when driven to pressurize medicament.

7. An apparatus as defined in claim 3, wherein each piston means includes a piston head fixed in a flexible wall of the vial for facilitating driving of the piston means.

8. An apparatus as defined in claim 2, wherein the outer nozzle forming member is made of a more flexible material in comparison to the inner nozzle forming member for facilitating opening of the interface in response to a flow of medicament of sufficient pressure for release through the nozzle into the eye.

9. An apparatus as defined in claim 3, wherein the outer nozzle forming member is made of a more flexible material in comparison to the inner nozzle forming member for facilitating opening of the interface in response to a flow of medicament of sufficient pressure for release through the nozzle into the eye.

10. An apparatus as defined in claim 7, wherein the outer nozzle forming member is an integral part of the flexible wall of the vial.

11. An apparatus as defined in claim 10, wherein the portion of the vial wall which comprises the outer nozzle forming member has a thickness which is thinner than the remainder of the vial wall for facilitating opening of the interface.

12. An apparatus as defined in claim 6, wherein each piston means includes a rim which makes contact with an inner surface of the respective piston cavity for facilitating pushing of medicament in the piston cavity into the interface during driving of the piston means.

13. An apparatus as defined in claim 1, further comprising a first medicament held in the first chamber and a second medicament, different from the first medicament, held in the second chamber.

14. An apparatus for simultaneously delivering a plurality of different medicaments to an eye without commingling of the different medicaments within the apparatus comprising:

a vial having an outer body which defines an outer nozzle forming section at an anterior end of the apparatus;

a means for partitioning the vial into a first medicament chamber and a second medicament chamber, said means for partitioning preventing commingling of medicament in the first chamber with medicament in the second chamber;

an inner nozzle forming body which is received within the outer nozzle forming section of the outer body, an outer surface of the inner nozzle forming body making surface to surface contact with an inner surface of the outer nozzle forming section of the outer body to define a normally closed interface terminating at an anterior nozzle tip, the closed interface preventing passage of medicament through the nozzle;

means defining a first drop cavity in fluid communication with the first medicament chamber;

means defining a second drop cavity in fluid communication with the second medicament chamber;

means for preventing commingling of medicament in the first drop cavity with medicament in the second drop cavity;

means for forcing a dosage of a first medicament in the first drop cavity to flow into and open the interface and to flow out of the apparatus through the nozzle; and means for forcing a dosage of a second medicament in the second drop cavity to flow into and open the interface and to flow out of the apparatus through the nozzle, whereby the interface immediately closes upon expulsion of said dosages of said first and second medicaments out of the nozzle thereby preventing reentry of medicament into the apparatus.

15. The apparatus according to claim 14, wherein the outer nozzle forming section is flexible relative to the inner nozzle forming body for facilitating opening of the interface and the nozzle in response to forced flow of dosages of medicament from the drop cavities.

16. The apparatus according to claim 14, wherein each means for forcing is a piston which is seated within the respective drop cavity and which is slideable in the respective drop cavity to push medicament from the drop cavity into the interface.

17. The apparatus according to claim 16, wherein the outer body of the vial is flexible and wherein each piston includes a piston head which is disposed within the outer body of the vial for facilitating driving of the pistons.

18. The apparatus according to claim 14, further comprising means defining a first channel between the first drop cavity and the interface and means defining a second channel between the second drop cavity and the interface, the first channel being isolated from the second channel.

19. The apparatus according to claim 14, wherein each drop cavity is dimensioned to release a predetermined volume of medicament into the eye.

* * * * *